US00PP18782P3

(12) United States Plant Patent
Bright et al.

(10) Patent No.: US PP18,782 P3
(45) Date of Patent: May 6, 2008

(54) PEACH-ALMOND HYBRID TREE NAMED 'ARTHUR V'

(50) Latin Name: *Prunus*
Varietal Denomination: Arthur V

(76) Inventors: William Bright, 5246 S. Plainsburg Rd., Le Grand, CA (US) 95333; Virginia Bright, 5246 S. Plainsburg Rd., Le Grand, CA (US) 95333; James Bright, 5246 S. Plainsburg Rd., Le Grand, CA (US) 95333; Edward Bright, 5246 S. Plainsburg Rd., Le Grand, CA (US) 95333

( * ) Notice: Subject to any disclaimer, the term of this patent is extended or adjusted under 35 U.S.C. 154(b) by 46 days.

(21) Appl. No.: 11/474,320

(22) Filed: Jun. 26, 2006

(65) Prior Publication Data

US 2007/0300336 P1 Dec. 27, 2007

(51) Int. Cl.
*A01H 5/00* (2006.01)

(52) U.S. Cl. ..... Plt./180

(58) Field of Classification Search ..... Plt./180
See application file for complete search history.

*Primary Examiner*—Kent Bell
*Assistant Examiner*—S. B. McCormick-Ewoldt

(57) ABSTRACT

The present invention relates to a peach-almond hybrid tree, *Prunus* sp., and more particularly to a new and distinct variety broadly characterized by a very large, extremely vigorous, hardy, self-sterile, productive and regular bearing tree. The fruit matures under the ecological conditions described in early September, with the first picking on Sep. 4, 2004. The tree is commercially useful as a rootstock for almost all *prunus* species. The variety was developed as a first generation cross using 'Titan' (unpatented) almond as the selected seed parent and 'Nemaguard' (unpatented) peach as the selected pollen parent.

1 Drawing Sheet

Botanical classification: *Prunus* sp.
Variety denomination: 'ARTHUR V'.

BACKGROUND OF THE VARIETY

In an effort to provide quality rootstocks for fruits and nuts, we, the inventors, typically hybridze a moderate number of almond seedlings each year. The present invention relates to a new and distinct variety of peach-almond hybrid tree, which has been denominated varietally as 'ARTHUR V'.

The present variety was hybridized by us in the spring of 1980, planted in our nursery that fall, and transplanted as one of about three thousand seedlings to one of our cultivated almond orchards the following winter near Le Grand, Calif. in Merced County (San Joaquin Valley). The variety was developed as a fruit generation cross using 'Titan' (unpatented) almond as the selected seed parent and 'Nemaguard' (unpatented) peach as the selected pollen parent. The crossing was accomplished by carefully isolating alternate trees of the 'Titan' almond, which is self-sterile, with the 'Nemaguard' peach, which was the only available pollen source. Over the years the present variety showed to be much more vigorous and healthier than its sister seedlings in the orchard described above, and was thus selected by us to multiply and further test as a potential rootstock. Subsequent to origination of the present variety of peach-almond hybrid tree, we asexually reproduced it using tissue culture techniques, and such reproduction of plant and fruit characteristics were true to the original plant in all respects. Such reproductions were transplanted into our test orchard located a few miles from the original tree and were carefully evaluated. After showing several outstanding characteristics, we determined the variety to have commercial value as a *prunus* rootstock.

The present variety is similar to its selected seed parent, 'Titan' almond by producing almonds that are sweet in flavor with a thin, well sealed shell, but is distinguished therefrom by using much more vigorous, by being more tolerant of calcareous soil conditions, by being somewhat resistant to root-knot nematode, and by having a more prolific root system for stronger anchorage.

The present variety is similar to its selected pollen parent, 'Nemaguard' peach, by acting as a rootstock for *prunus* varieties that is somewhat resistant to root-knot nematode, that is not very tolerant of heavier soils and excess water, and that is susceptible to crown gall, oak-root fungus, phytophthora, bacterial canker and crown rot, but is distinguished therefrom by having a much stronger root system, by being more drought tolerant, and by being much more vigorous to provide better growth in marginal soils.

The variety is most similar to 'Hansen 2168' (U.S. Plant Pat. No. 5,210) by being a peach almond hybrid tree that is utilized primarily as a rootstock for *prunus* varieties that is vigorous, nematode resistant, deep rooting and drought tolerant, but is distinguished therefrom by having globose glands, by blooming later, by having fruit that matures in September instead of August, by having light yellow green flesh toward the stone instead of red, and by having a sweet kernel that can be used as an almond for human consumption instead of a bitter kernel.

SUMMARY OF VARIETY

In summary, the present variety is characterized by a very large size, extremely vigorous, hardy, self-sterile, productive and regular bearing tree. The nut matures under the ecological conditions described in early September, with the harvest date on Sep. 4, 2004. The tree is most useful for a commercial rootstock, which has shown to be compatible with all tested almonds, peaches and nectarines. The tree has also shown to be drought tolerant, has a strongly developed root system, and has proven to exhibit resistance to nematodes, while being susceptible to crown rot, phytophthora, oak root fungus, crown gall, and bacterial canker.

DRAWING

The accompanying photograph exhibits three whole fruits positioned to display the characteristics of the skin color and form, two fruits divided along the suture plane to reveal the flesh and stone, one stone removed from the flesh, two kernels, and typical leaves. The photograph also includes an inset revealing various stages of the bloom.

POMOLOGICAL CHARACTERISTICS

Referring now more specifically to the pomological characteristics of this new and distinct variety of peach-almond hybrid tree, the following has been observed under the ecological conditions prevailing near Le Grand, Merced County (San Joaquin Valley), Calif. The fruit description was developed one week before harvest on Aug. 27, 2004, and the flower description on Mar. 5, 2004, on a cloned tree located in our test orchard described above during its fifth growing season. The tree description was developed from the original tree during its twenty-fifth growing season. All major color code designations are by reference to the Inter-Society Colour Council, National Bureau of Standards. Common color names are also used occasionally.

Tree

Size: Very large, reaching a height of 35' [10.67 m.] and a spread of 24' [7.32 m.] after twenty-five growing seasons utilizing minimal dormant pruning.

Vigor: Extremely vigorous. The variety grows about 2' [0.61 m.] of top-growth during the spring and summer.

Growth: Upright and dense.

Form: Vase formed.

Hardiness: Hardy with respect to central California winters.

Heat tolerance: Observed to perform adequately in typical central. California climatic conditions, which typically include extended periods of heat.

Drought tolerance: Variety requires regular irrigation, but is more tolerable to drought conditions than most varieties.

Production : Productive.

Fertility: Self-sterile, but may be cross pollinated by 'Nonpareil' (unpatented) almond.

Bearing: Regular bearer.

Trunk:

- *Size.*—Large, with a maximum diameter of 20" [508 mm.] after the twenty-fifth growing season.
- *Texture.*—Medium.
- *Bark color.*—Dark grayish brown [62. d.gy.Br].
- *Lenticels.*—Approximate Number Per Square Inch: 5. Color: Strong yellowish brown [74. s.yBr]. Average Size: 7/16" [11.1 mm.]. Shape: Elongated to eye-shaped.

Branches:

- *Size.*—Diameter of limb is 12" [305 mm.] measured 12" above the crotch, typical of *Prunus* species, and dependent upon cultural practices and climatic conditions.
- *Texture.*—Medium.
- *Color.*—1st Year Wood Topside: Grayish red [19. gy.R]. 1st Year Wood Underside: Brilliant yellow green [116. brill.YG]. Older Wood: Dark grayish brown [62. d.gy.Br].
- *Lenticels.*—Approximate Number Per Square Inch: 20. Color: Light grayish yellowish brown [79. l.gy.yBr]. Typical size: 1/8" [3.2 mm.] to 1/4" [6.4 mm.]. Shape: Elongated to eye-shaped.

Leaves:

- *Size.*—Medium. Average Length: 4½" [114 mm.]. Average Width: 1¼" [31.8 mm.].
- *Arrangement.*—Alternate.
- *Thickness.*—Medium.
- *Form.*—Elliptical.
- *Apex.*—Acuminate.
- *Base.*—Rounded to slightly acute.
- *Surface.*—Smooth.
- *Color.*—Dorsal Surface: Deep yellow green [118. deep YG]. Ventral Surface: Moderate olive green [125. m.OlG].
- *Margin.*—Finely serrate.
- *Venation.*—Pinnately net veined.
- *Vein color.*—Light yellow green [119. l.YG] with some Dark red [16. d.R] tinting.
- *Petiole.*—Average Length: 11/16" [17.5 mm.]. Average Thickness: 1/16" [1.6 mm.]. Color: Dark red [16. d.R] topside, Light yellow green [119. l.YG] underside.
- *Stipules.*—Number: Up to 6 per growing tip. Average Length: 1/4" [6.4 mm.]. Color: Strong yellow green [117. s.YG] becoming Dark reddish brown [44. d.rBr] with maturity.
- *Glands.*—Number: Usually 2 to 4. Position: Mostly alternate. Size: Small. Form: Globose. Color: Light yellow green [119. l.YG] becoming Moderate reddish brown [43. m.rBr] with age.
- *Leaf Buds.*—Small, pointed, Dark grayish brown [62. d.gy.Br].

Flower buds:

- *Hardiness.*—Hardy, with respect to central California winters.
- *Diameter.*—Typically 5/16" [7.9 mm.] 1 week before bloom.
- *Length.*—Typically 7/16" [11.1 mm.] 1 week before bloom.
- *Form.*—Not appressed.
- *Surface.*—Pubescent.
- *Color.*—Light pink [4. l.Pk].

Flowers: Perfect, complete, perigynous, usually a single pistil, typically thirty or more stamens, five sepals and petal locations alternately positioned.

- *Type.*—Showy.
- *Average flower diameter.*—1¼" [31.8 mm.].
- *Number of petals.*—Predominately five.
- *Petal shape.*—Oval.
- *Petal margin.*—Somewhat wavy.
- *Average petal diameter.*—½" [12.7 mm.].
- *Average petal length.*—5/8" [15.9 mm.].
- *Petal apex.*—Rounded with a small notch on most.
- *Petal base.*—Rounded to obtuse.
- *Petal color.*—Pinkish white [9. pkWhite].
- *Anther color.*—Moderate reddish orange [37. m.rO] over Pale yellow [89. p.Y] centers.
- *Stigma color.*—Pale greenish yellow [104. p.gY].
- *Sepal color.*—Very yellow green [115. v.YG] with varying degrees of Dark purplish red [259. d.pR] streaking.
- *Sepal length.*—1/4" [6.4 mm.].
- *Sepal width.*—3/16" [4.8 mm.].

*Average pistil length.*—9/16" [14.3 mm.].
*Average stamen length.*—1/2" [12.7 mm.].
*Fragrance.*—Moderate.
*Blooming period.*—Medium compared with typical almond varieties.
*Onset of bloom.*—One percent on Feb. 28, 2004.
*Date of full bloom.*—Mar. 9, 2004.
*Duration of bloom.*—One to two weeks, dependent on ambient temperature.
*Number per cluster.*—1 to 3 with single flowers most common.

FRUIT

Maturity when description: Hard ripe, Aug. 27, 2004.
Date of harvest: Sep. 4, 2004.
Size: Uniform.
*Average diameter axially.*—1 3/8" [34.9 mm.].
*Average diameter across suture plane.*—1 1/8" [28.6 mm.].
*Typical weight.*—2.6 ounces [74 grams].
Form: Uniform, symmetrical and oblong.
*Longitudinal section form.*—Oval.
*Transverse section through diameter.*—Round.
Suture: A distinct sharp groove from apex to stem deepening and splitting with maturity, extends from base to pistil point.
Ventral surface: Rounded, lipped throughout slightly stronger on the side.
Lips: Slightly unequal.
Cavity: Flaring, circular, suture showing on one side.
*Depth.*—3/16" [4.8 mm.].
*Breadth.*—5/16" [7.9 mm.].
Base: Rounded.
Apex: Rounded to slightly truncate.
Pistil point: Apical, very short.
Stem: Medium.
*Average length.*—3/8" [9.5 mm.].
*Average width.*—3/16" [4.8 mm.].
Skin:
*Thickness.*—Thick.
*Surface.*—Tough.
*Tenacity.*—Tenacious to flesh.
*Astringency.*—Astringent.
*Tendency to crack.*—Only along the suture with maturity.
*Color.*—Grayish yellow green [122. gy.YG] on the tree, Grayish greenish yellow [105. gy.gy] when dried.
Flesh:
*Color.*—Light yellow green [119. l.YG] toward the stone, Moderate yellow green [120. m.YG] toward the skin.
*Surface of pit cavity.*—Freestone, Light yellow green [119 l.YG] to Pale yellow green [121. p.YG] when first opened turning Strong brown [55. s.Br] within an hour.
*Amygdalin.*—Scarce.
*Juice.*—Very scant.
*Texture.*—Firm, tough.
*Fibers.*—Abundant, tough.
*Ripens.*—Evenly.
*Flavor.*—Bland.
*Aroma.*—Wanting.

STONE

Type: Freestone.
Form: Oval.
Hilum: Narrow, oval.
Base: Slightly oblique.
Apex: Obtuse, 90 to 105 degrees.
Sides: Equal.
Surface: Pitted throughout the characteristic grooves on each side of the dorsal fin.
External color: Pale orange yellow [73. p.OY].
Cavity surface color: Pale orange yellow [73. p.OY].
Average pit wall thickness: 3/32" [2.4 mm.].
Average width: 11/16" [17.5 mm.].
Average length.1 1/8" [28.6 mm.].
Average breadth: 5/8" [15.9 mm.].
Tendency to split: None.
Kernel:
*From.*—Oval.
*Skin color.*—Light orange yellow [70. l.OY] when freshly cracked and Dark reddish brown [44. d.rBr] when dried.
*Pellicle color.*—Deep yellowish brown [75. deep yBr].
*Vein color.*—Deep yellowish brown [75. deep yBr].
*Taste.*—Sweet.
*Viable.*—Yes.
*Average width.*—1/2" [12.7 mm.].
*Average length.*15/16" [23.8 mm.].
*Amygdalin.*—Scant.

USE

Rootstock: Can be used as a rootstock for almost all *prunus* varieties.
Flesh: Can be used for cattle feed when dry.
Kernel: Can be used as an almond for human consumption.
Resistance to pests: Very resistant to nematodes.
Resistance to diseases: Somewhat susceptible to bacterial canker, crown gall, oak root fungus, and phytophthora.

Other Notes

Although the new variety of peach-almond hybrid tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach-almond hybrid tree, substantially as illustrated and described, that is most similar to 'Hansen 2168' (U.S. Plant Pat. No. 5,210) by being a peach almond hybrid tree that is utilized primarily as a rootstock for *prunus* varieties that is vigorous, nematode resistant, deep rooting and drought tolerant, but is distinguished therefrom by having globose glands, by blooming later, by having fruit that matures in September instead of August, by having light yellow green flesh toward the stone instead of red, and by having a sweet kernel that can be used as an almond for human consumption instead of a bitter kernel.

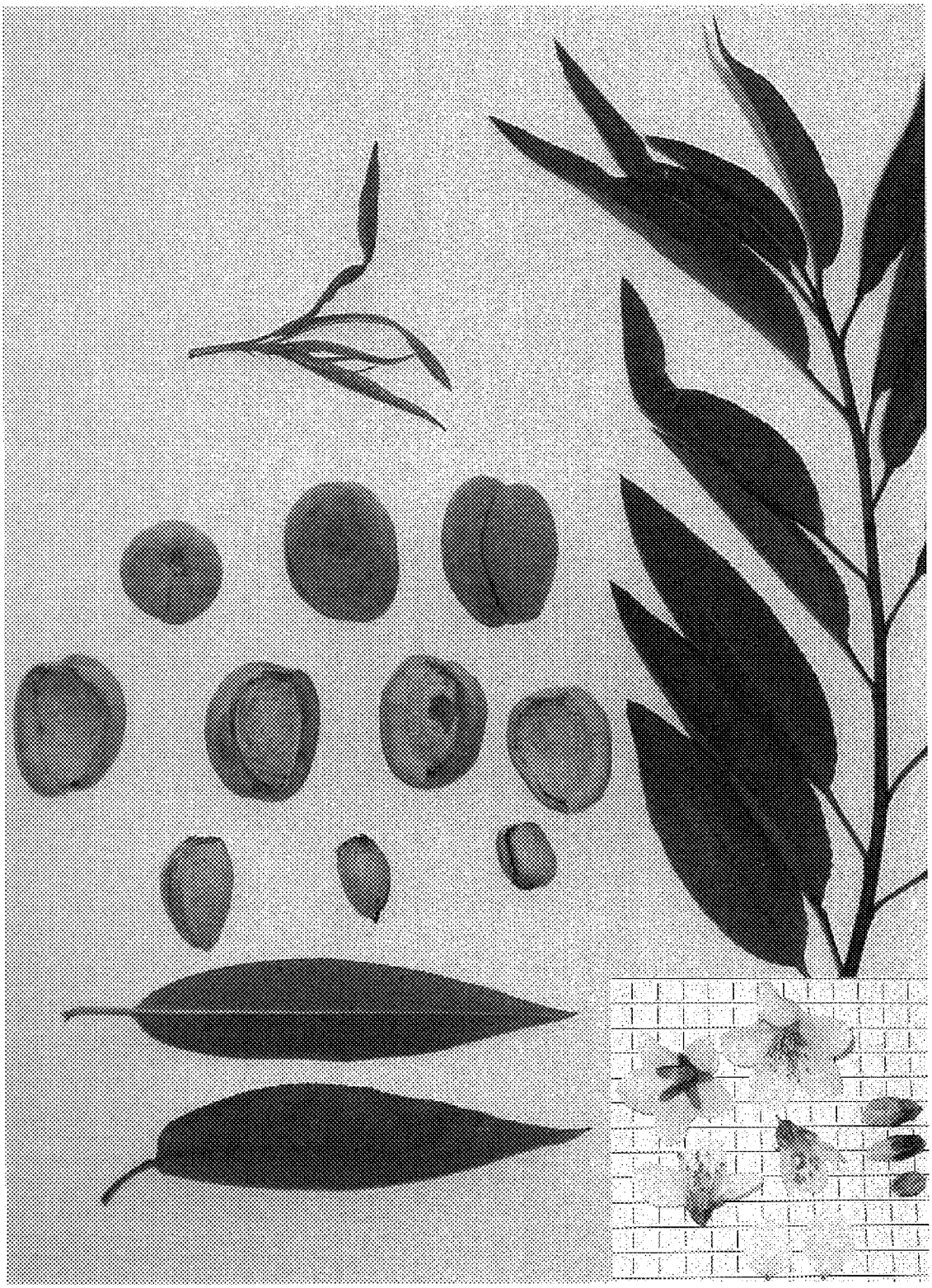

* * * * *